(12) United States Patent
Yamamoto et al.

(10) Patent No.: US 7,557,226 B2
(45) Date of Patent: Jul. 7, 2009

(54) PROCESS FOR PRODUCING CUMENE

(75) Inventors: Jun Yamamoto, Sodegaura (JP); Masaaki Katao, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 666 days.

(21) Appl. No.: 10/571,471

(22) PCT Filed: Sep. 10, 2004

(86) PCT No.: PCT/JP2004/013587
§ 371 (c)(1),
(2), (4) Date: Mar. 13, 2006

(87) PCT Pub. No.: WO2005/028405
PCT Pub. Date: Mar. 31, 2005

(65) Prior Publication Data
US 2006/0258892 A1    Nov. 16, 2006

(30) Foreign Application Priority Data

Sep. 18, 2003  (JP) ............................. 2003-325742
Sep. 18, 2003  (JP) ............................. 2003-325743

(51) Int. Cl.
*C07D 301/19* (2006.01)
*C07C 1/22* (2006.01)
*C07C 1/24* (2006.01)

(52) U.S. Cl. ....................................... 549/529; 585/469

(58) Field of Classification Search .................. 549/529; 585/469
See application file for complete search history.

(56) References Cited

U.S. PATENT DOCUMENTS

| 3,441,618 A | 4/1969 | Flickinger |
| 6,153,153 A | 11/2000 | Jubin, Jr. et al. |
| 2006/0183926 A1 | 8/2006 | Tsuji et al. |

FOREIGN PATENT DOCUMENTS

| EP | 1 266 891 A | 12/2002 |
| EP | 1 266 893 A1 | 12/2002 |
| GB | 1 122 702 A | 8/1968 |
| JP | 2001-270878 A | 10/2001 |
| JP | 2004-250430 A | 9/2004 |
| WO | WO 99/58480 A | 11/1999 |
| WO | WO 2004/058667 A1 | 7/2004 |

OTHER PUBLICATIONS

XP002426272 corresponds to JP 56-140933 A, published Nov. 4, 1981.
European Chemicals News, Mar. 5-11, 2001, vol. 74, No. 1974, pp. 3, 19-20.

*Primary Examiner*—Bernard Dentz
(74) *Attorney, Agent, or Firm*—Sughrue Mion, PLLC

(57) ABSTRACT

A process for the production of cumene, which comprises producing cumene from cumyl alcohol and hydrogen with a dehydration catalyst and a hydrogenation catalyst, wherein the dehydration catalyst and hydrogenation catalyst are alternately packed so as to form n layers (n is an integer of 3 or more) or are packed as a mixture thereof in a reactor.

6 Claims, No Drawings

PROCESS FOR PRODUCING CUMENE

TECHNICAL FIELD

The present invention relates to a process for producing cumene. More particularly, the present invention relates to a process for producing cumene, which can efficiently produce cumene at low cost.

BACKGROUND ART

There is publicly known a process for producing cumene by dehydrating cumyl alcohol in the presence of a dehydration catalyst to convert into α-methyl styrene, subsequently hydrogenating α-methyl styrene in the presence of a hydrogenation catalyst to convert into cumene (for example, European Chemical News, Volume 74, Number 1947, 5-11, March 2001). However, the publicly known process could not be necessarily satisfied from the viewpoint of efficient production of cumene at low cost.

DISCLOSURE OF THE INVENTION

The present invention is to provide a process for efficiently producing cumene at low cost.

Namely, the present invention relates to a process for the production of cumene, which comprises producing cumene from cumyl alcohol and hydrogen with a dehydration catalyst and a hydrogenation catalyst, wherein the dehydration catalyst and hydrogenation catalyst are alternately packed so as to form n layers (n is an integer of 3 or more) or are packed as a mixture thereof in a reactor.

BEST MODE FOR CARRYING OUT THE INVENTION

In the present invention, production of α-methyl styrene through dehydration of cumyl alcohol and production of cumene through hydrogenation of said α-methyl styrene are conducted in one reactor. In other words, cumene is produced from cumyl alcohol via α-methyl styrene.

The dehydration is a reaction for converting into α-methyl styrene and water through dehydration of cumyl alcohol in the presence of the dehydration catalyst.

As the dehydration catalyst, there are listed metal oxides such as activated alumina, titania, zirconia and silica-alumina, and activated alumina is preferred from viewpoints of catalyst life, selectivity and the like.

The hydrogenation is a reaction for converting into cumene by supplying α-methyl styrene and water obtained by dehydration in the hydrogenation catalyst thereby hydrogenating α-methyl styrene.

As the hydrogenation catalyst, a catalyst containing a metal of Group 10 or 11 of the Periodic Table of the Elements, can be listed, and, specifically, nickel, palladium, platinum and copper are listed. But, from viewpoints of suppression of nuclear hydrogenation of an aromatic ring and high yield, palladium and copper are preferable, further among these, palladium is the most preferable. Copper-based catalysts include copper, Raney copper, copper-chromium, copper-zinc, copper-chromium-zinc, copper-silica, copper-alumina and the like. Palladium-based catalysts include palladium-alumina, palladium-silica, palladium-carbon and the like.

In the present invention, a fixed bed reactor is usually used.

The dehydration and hydrogenation can be respectively conducted in a liquid phase using a solvent. The solvent should be substantially inert to reactants and products. The solvent may be a substance contained in a solution to be used. For example, when cumyl alcohol is a mixture with cumene as a product, it is possible to use cumene as a substitute without adding a solvent in particular.

As other useful solvents, there can be listed alkanes (e.g. octane, decane, dodecane), mono-cyclic aromatic compound (e.g. benzene, ethylbenzene, toluene) and the like.

The feature of the invention is, in a process for producing cumene from cumyl alcohol and hydrogen with the dehydration catalyst and hydrogenation catalyst, that the dehydration catalyst and hydrogenation catalyst are alternately packed in a reactor so as to form n layers (n is an integer of 3 or more) or packed as a mixture thereof in a reactor.

Preferable embodiments thereof are as follows:

The dehydration catalyst and hydrogenation catalyst are alternately packed in a fixed bed reactor so as to form n layers (n is an integer of 3 or more). When the dehydration catalyst and hydrogenation catalyst are alternately packed so as to form layers of 3 or more, it is advantageous compared to two layers in points described below.

As a reactor used, though there are an adiabatic reactor and isothermal reactor, the adiabatic reactor is preferred because the isothermal reactor requires an equipment for heat removal. In a case of the adiabatic reactor, the temperature lowers with progress of the reaction because the dehydration of cumyl alcohol is an endothermic reaction, and, on the other hand, since the hydrogenation of α-methyl styrene is an exothermic reaction, the temperature rises with progress of the reaction. The outlet temperature becomes higher than the inlet temperature because the generated heat quantity is larger in total.

In the two-layer packing, because the hydrogenation as an exothermic reaction is conducted after the dehydration reaction as an endothermic reaction is almost completed, there are appeared adverse effects that the temperature difference between a low temperature part and high temperature part becomes very large, for this reason, the rate of dehydration reaction lowers at the low temperature part or a side reaction beyond the purpose is accelerated by rapid rise of the temperature at the high temperature part.

In a case of packing of three layers or more, the temperature distribution in the reactor is smoothed since the hydration as the endothermic reaction and the hydrogenation as the exothermic reaction are conducted alternately and gradually, and, the above-described adverse effect is reduced compared to the two layers packing.

Examples of 3 layers or more include 4 layers packing of a dehydration catalyst, hydrogenation catalyst, dehydration catalyst and hydrogenation catalyst in this order from the inlet of the reactor, and 6 layers packing of a dehydration catalyst, hydrogenation catalyst, dehydration catalyst, hydrogenation catalyst, dehydration catalyst and hydrogenation catalyst in this order from the inlet of the reactor, but are not restricted thereto.

The number of the layer is more preferably an even number of 4 or more because the dehydration catalyst as the inlet layer and the hydrogenation catalyst as the final layer are usually preferred. It is not necessary that, when there are respectively a plurality of layer of the dehydration catalyst and/or hydrogenation catalyst, all of layers in respective catalysts are similar, but it is preferable that those are similar.

Further, it is not necessary that the inlet part of the reactor is the dehydration catalyst, and another catalyst may be packed for a purpose of other than dehydration of cumyl alcohol. Furthermore, it is not necessary that the catalyst amounts of respective layers are equivalent, and the amounts can be arbitrarily selected depending on properties of dehydration and hydrogenation. Moreover, as another embodiment, there is a method in which a mixed catalyst of the dehydration catalyst and hydrogenation catalyst is packed in a reactor.

In this method, since the dehydration as an endothermic reaction and the hydrogenation as an exothermic reaction are apparently conducted in parallel, the temperature distribution inside the reactor is more smoothed, in comparison with the two-layer packing, leading to reduction of the above-described adverse effect.

The dehydration catalyst and the hydrogenation catalyst in the mixed catalyst are not necessarily uniform in mixed ratio over the whole reactor, and the mixed ratio can be properly selected depending on properties of the dehydration catalyst and the hydrogenation catalyst.

Further, in the present invention, in addition to layers of the dehydration catalyst and the hydrogenation catalyst, a mixed layer thereof may be set up.

The total amount of the dehydration catalyst to be packed in the reactor may be an amount so that cumyl alcohol is sufficiently converted into α-methyl styrene, and the conversion of cumyl alcohol in the whole of the reactor is preferably 90% or more. Similarly, the total amount of the hydrogenation catalyst to be packed in the reactor may be an amount so that α-methyl styrene is sufficiently converted into cumene, and the conversion of α-methyl styrene in the whole of the reactor is preferably 98% or more.

The reaction temperature and pressure are selected so that water in the solution is not condensed. The reaction temperature is preferably 150 to 300° C., and the reaction pressure is preferably 100 to 2000 kPa. When the reaction temperature is too low or the reaction pressure is too higher, water may be condensed leading to deterioration of the performance of the hydrogenation catalyst. Further, when the pressure is too high, it is also disadvantageous in the reaction equilibrium of dehydration. When the temperature is too high or the pressure is too low, it may become disadvantageous because the catalyst life is shortened by fouling or the like caused by much generation of the gas phase part.

In the present invention, the operation range of the reaction temperature and reaction pressure is wide because the temperature distribution inside the reactor is more smoothed compared to the two-layer packing, therefore, the present invention is also advantageous from the above-described viewpoint.

In the present invention, a side-reaction derived from α-methyl styrene (for example, production of a dimer of α-methyl styrene) can be suppressed since the concentration of α-methyl styrene in the reactor can be controlled lower in addition to smoothing of the temperature distribution.

Hydrogen can be supplied from any of inlets of the reactor and inlets of the hydrogenation catalyst, and it is preferable to supply from the inlet of the reactor. That is, vaporization of water produced through dehydration is promoted by bringing into anytime existence of hydrogen in the dehydration zone and the equilibrium dehydration conversion rises, therefore, high conversion can be attained effectively compared to absence of hydrogen.

Though water generated in the dehydration is passed through the hydrogenation catalyst, it is possible to operate at low cost without particularly setting up an apparatus for water removal as described above, by operating at the level not condensing water.

The amount of hydrogen required in the reaction may be equimolar to α-methyl styrene produced by the dehydration, but the excess amount of hydrogen is usually required because other components consuming hydrogen are contained in the raw material. Further, the molar ratio of hydrogen to α-methyl styrene of 1 to 10 is adopted from a reason why the reaction proceeds faster with rising of a partial pressure of hydrogen. It is further preferably 1 to 5. Hydrogen in an excess amount remained after the reaction, can be recycled and used after separated from the reaction mixture.

The process of the present invention is preferably applied to a dehydration step and hydrogenation step of a production process of propylene oxide containing the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene;

dehydration step: a step of obtaining α-methyl styrene by dehydrating cumyl alcohol obtained in the epoxidation step in the presence of a dehydration catalyst;

hydrogenation step: a step of obtaining cumene by hydrogenation of α-methyl styrene in the presence of a hydrogenation catalyst; and recycling step: recycling cumene obtained in the hydrogenation step to the oxidation step.

The oxidation step is a step for obtaining cumene hydroperoxide by oxidizing cumene. The oxidation of cumene is usually conducted by auto-oxidation using an oxygen-containing gas such as air or oxygen-concentrated air. This oxidation may be conducted without use of an additive, and an additive such as an alkali may be used.

The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, or alkali metal carbonate such as $Na_2CO_3$ or $NaHCO_3$, ammonia, $(NH_4)_2CO_3$, an alkali metal ammonium carbonate or the like, is used as the alkali reagent.

The epoxidation step is a step for obtaining propylene oxide and cumyl alcohol by reacting cumene hydroperoxide obtained in the oxidation step with propylene.

As a catalyst, catalysts containing titanium-containing silicon oxide, are preferable from the viewpoint of obtaining the objective product under high yield and high selectivity. As these catalysts, so-called Ti-silica catalysts containing Ti chemically bonded to silicon oxide, are preferable. For example, a catalyst prepared by supporting a Ti compound on a silica carrier, a catalyst prepared by combining a Ti compound with silicon oxide by a coprecipitation method or sol gel method, zeolite compounds containing Ti, and the like, can be listed.

Cumene hydroperoxide used as a raw material in the epoxidation step may be a dilute or dense purified material or non-purified material.

The epoxidation is conducted by contacting propylene and cumene hydroperoxide with the catalyst. The reaction is carried out in a liquid phase using a solvent. The solvent should be liquid under a temperature and pressure in the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent. Additionally, mono-cyclic aromatic compounds (e.g. benzene, toluene, chlorobenzene, orthodichlorobenzene), alkanes (e.g. octane, decane, dodecane) and the like, can be listed as useful solvents.

The epoxidation temperature is usually from 0 to 200° C., and preferably from 25 to 200° C. The pressure may be a pressure sufficient to keep the reaction mixture in a liquid condition. In general, the pressure is advantageously from 100 to 10000 kPa.

When a solid catalyst is used, it is used for the reaction in the form of a slurry or fixed bed. In the case of a large-scale industrial operation, a fixed bed is preferably used. In addition, the epoxidation can be conducted by a batch-wise method, a semi-continuous method or a continuous method.

The molar ratio of propylene to cumene hydroperoxide supplied to the epoxidation step, is preferably 2/1 to 50/1. When the ratio is 2/1 or more, the efficiency is good because the reaction rate does not decrease, on the other hand, when the ratio is 50/1 or less, large energy in recycling is not required because the amount of propylene to be recycled does not become bigger.

The dehydration and hydrogenation steps are steps for obtaining α-methyl styrene by dehydrating cumyl alcohol obtained in the epoxidation step and subsequently obtaining cumene by hydrogenating it, respectively, as the before-mentioned.

EXAMPLE

Catalysts described below was used in Comparative Example 1 and Example 1:
Catalyst A: activated alumina (pulverized product:0.5-0.85 mm)
Catalyst B: 0.05 wt %Pd/alumina (pulverized product:0.5-0.85 mm)

Comparative Example 1

Two-layer Packing

The catalyst A of 3 m-thick as a first layer and the catalyst B of 1.2 m-thick as a second layer were packed in a reactor having an inner diameter of 4 mmφ. The first layer and second layer were heated to 230° C. and 190° C., respectively, and 0.1 normal liter/minute of hydrogen and 1.6 g/minute of a cumene solution having a cumyl alcohol concentration of 23% by weight under a pressure of 1.4 MPa-G, were simultaneously fed to the reactor, continuously. After the reaction of 109 hours, a cumyl alcohol conversion was 99.8% and a selectivity of a cumene dimer (hydrogenated product of an α-methyl styrene dimer) was 0.9%.

Further, a concentration of α-methyl styrene in cumene obtained was less than 0.01% by weight.

Example 1

Multi-Layer Packing

The catalyst B of 0.1 m-thick as a first layer, the catalyst A of 0.2 m-thick as a second layer, the catalyst B of 0.4 m-thick as a third layer, the catalyst A of 0.4 m-thick as a fourth layer, the catalyst B of 0.4 m-thick as a fifth layer, the catalyst A of 2.4 m-thick as a sixth layer and the catalyst B of 0.4 m-thick as a seventh layer (catalyst A: 3 m-thick in total, catalyst B: 1.3 m-thick in total) were packed in a reactor having an inner diameter of 4 mmφ. The first and second layers, the third to fifth layers, and the sixth and sevens layers were heated to 180° C., 200° C. and 230° C., respectively, and 0.1 normal liter/minute of hydrogen and 1.6 g/minute of a cumene solution having a cumyl alcohol concentration of 23% by weight under a pressure of 4 MPa-G, were simultaneously fed to the reactor, continuously. After the reaction of 88 hours, a cumyl alcohol conversion was 99.9% and a selectivity of a cumene dimer was 0.2%.

Further, a concentration of α-methyl styrene in cumene obtained was less than 0.01% by weight.

INDUSTRIAL APPLICABILITY

As described above, according to the present invention, there can be provided a process for producing effectively cumene at low cost. In addition, the present process can be suitably applied to production of propylene oxide.

The invention claimed is:

1. A process for the production of cumene, which comprises producing cumene from cumyl alcohol and hydrogen with a dehydration catalyst and a hydrogenation catalyst, wherein the dehydration catalyst and hydrogenation catalyst are alternately packed so as to form n layers (n is an integer of 3 or more) or are packed as a mixture thereof in a reactor.

2. The process according to claim 1, wherein n is an even number of 4 or more.

3. The process according to claim 1, wherein the dehydration catalyst is activated alumina.

4. The process according to claim 1, wherein the hydrogenation catalyst is a catalyst containing a metal of Group 10 or 11 of the Periodic Table.

5. The process according to claim 4, wherein the metal is palladium.

6. A process for producing propylene oxide, which comprises the following steps:
 oxidation step: a step of obtaining cumene hydroperoxide by oxidizing cumene;
 epoxidation step: a step of obtaining propylene oxide and cumyl alcohol by reacting cumene hydroperoxide obtained in the oxidation step with propylene;
 dehydration step: a step of obtaining α-methyl styrene by dehydrating cumyl alcohol obtained in the epoxidation step in the presence of a dehydration catalyst;
 hydrogenation step: a step of obtaining cumene by hydrogenating α-methyl styrene in the presence of a hydrogenation catalyst; and
 recycling step: recycling cumene obtained in the hydrogenation step to the oxidation step, wherein the dehydration and the hydrogenation steps are the process according to any one of claims 1 to 5.

* * * * *